(12) United States Patent
Hellberg

(10) Patent No.: US 6,440,345 B1
(45) Date of Patent: Aug. 27, 2002

(54) METHOD FOR CREATING A SLEEVE MEMBER ATTACHED TO A BODY PORTION

(75) Inventor: Kennet Hellberg, Vallentuna (SE)

(73) Assignee: Centri AB, Jarfalla (SE)

( * ) Notice: Subject to any disclaimer, the term of this patent is extended or adjusted under 35 U.S.C. 154(b) by 0 days.

(21) Appl. No.: 09/403,077

(22) Filed: Oct. 15, 1999

(30) Foreign Application Priority Data

Apr. 29, 1997 (SE) ................................................ 9701619

(51) Int. Cl.⁷ ................................................ B29C 33/40
(52) U.S. Cl. .......................................... 264/222; 623/36
(58) Field of Search .................... 623/33, 36; 264/222, 264/DIG. 30

(56) References Cited

U.S. PATENT DOCUMENTS

| | | | |
|---|---|---|---|
| 4,473,421 A | | 9/1984 | Gustafsson |
| 4,685,453 A | * | 8/1987 | Guignard et al. ........... 264/222 |
| 4,696,780 A | | 9/1987 | Hägglund |
| 5,376,132 A | * | 12/1994 | Caspers ........................ 623/36 |
| 5,603,122 A | | 2/1997 | Kania |
| 5,662,715 A | * | 9/1997 | Slemker ........................ 623/36 |
| 5,830,237 A | | 11/1998 | Kania |

FOREIGN PATENT DOCUMENTS

| | | | |
|---|---|---|---|
| GB | 2104386 | * 3/1983 | .................. 623/36 |
| SE | 454943 | * 6/1988 | |
| WO | 9703819 | 2/1997 | |

OTHER PUBLICATIONS

Abstract of patent SE–434928 published Aug. 1984 to Elofsson et al.*

* cited by examiner

*Primary Examiner*—Paul Prebilic
(74) *Attorney, Agent, or Firm*—Young & Thompson

(57) ABSTRACT

A method for creating a flexible sleeve member for an amputation stump. The sleeve member is made of a thermoplastic elastic and transparent material. The sleeve member is shaped after a flexed limb, for instance a knee, which makes it easier to avoid foldings of the sleeve, which would otherwise be obtained at the back of the knee when a person wearing the prosthetic device sits down. By means of the sleeve member according to the invention, comfort is improved for a person wearing such a prosthetic device.

3 Claims, 3 Drawing Sheets

METHOD FOR CREATING A SLEEVE MEMBER ATTACHED TO A BODY PORTION

TECHNICAL FIELD

The present invention relates to a prosthetic sleeve, and more exactly a sleeve member intended to be adapted to and attached to a body portion like an amputation stump.

BACKGROUND OF THE INVENTION

In connection with amputation of an extremity e.g. a leg, a so called amputation stump is normally kept, that is to say some portion of the amputated extremity is left to serve as an attachment for a suitable prosthesis.

A suitably adapted sleeve member is slipped over the remaining stump and constitutes in this way a fastening for the real prosthetic device, which for example may be a foot or a lower leg with foot in case the stump is situated below the knee of a leg. Similarly the prosthesis may be an entire prosthetic leg, whereby a remaining portion of the thigh bone is fitted into a corresponding prosthetic sleeve. In a corresponding way a lower arm or an upper arm prosthesis is attached.

Such a sleeve member consists of a conical shape, one end of which is open and the other is completely closed and having a somewhat rounded off shape. Additionally the sleeve member is plastic to be adapted to an amputation stump.

In conventional provisions of prosthetic devices for, e.g. an amputated extremity, it is consequently confining what is left of the extremity in a specially adapted sleeve attached to the prosthesis, transferring forces between the prosthesis and the remaining portion of the extremity.

A specially adapted sleeve is made by producing an exact copy of what is left of this extremity. Today there are mainly two methods utilized to do this, either a laser scanner is used which is imaging the body portion to be copied, then the values read by the scanner are transferred to a milling cutter, which mills a copy of the body portion, or a negative plaster cast is made by means of plaster bandage, whereafter the negative plaster cast is filled to create an exact positive copy of the body portion. Then by means of the positive copy a normally rigid prosthetic sleeve is molded, which may be placed onto the amputation stump. The disadvantage with such copies is that they are exact only at the time of the plaster casting. The reason for this is that the human body is continuously changing and especially then the portion left of an amputated extremity, the atrophy being large (in time it decreases in volume).

The problem of the rigid sleeve is that it does not follow the changes in volume and what is left of the extremity is soft and sensitive while the sleeve member is hard, which easily results in being chafed if there is not a softer sleeve inside the rigid sleeve. Therefore today some different kinds of soft sleeves are made to be used with such rigid outer sleeves.

Today a commonly found soft sleeve is an American product which is normally referred to as the Alpha sleeve. The Alpha sleeve is made from a thick thermoplastic elastic material, which was necessary to reinforce by an outer layer of fabric. The advantage of the Alpha sleeve is that it is possible to adapt it to a certain extent to the stump of the patient, which means that many problems are avoided. The drawback is that it must be reinforced by the outer layer of fabric, which implies that the stump cannot be seen through the sleeve. If the stump cannot be seen through the sleeve it is not possible to decide if the sleeve is correctly adapted. If a specifically adapted sleeve is incorrectly placed the pressure stress at dangerous spots may be increased. Additionally it is not seen whether a decreased stress is to be arranged over some prominence. Furthermore it is not simple to attach a stress-relief to the Alpha sleeve due to the layer of fabric. The layer of fabric also limits the adaptability, the fabric may only be stretched to a certain limit, and a small uneven stress over the prominences will be introduced.

Today another frequently found inner sleeve is one made of silicone and disclosed in the Swedish Patent document SE 454 943. The problem of this sleeve is that it is not able to be particularly adapted to the amputation stump. The sleeve instead is so elastic that it can encircle the amputation stump, but as no amputation stump in reality is shaped conically, there will be higher pressure and stress onto the following portions of the stump:

In areas where the diameter of the stump is larger than the silicone sleeve, which means that the surface pressure will be higher to the stump in this area compared to other areas.

In areas, where the stump has a small radius, e.g. a prominence due to underlying bone, which means that the surface pressure over the prominence itself locally increases when the elastic sleeve is tightened over the prominence. Also see example of FIG. 4, which symbolizes an elastic sleeve rolled onto a stump of a lower leg amputee, illustrating how the distal tibia point creates a bone prominence downmost to the left in FIG. 4, which is a common view.

Not only the pressure at these exposed portions will increase, but with this stretching of the sleeve in these more sensitive areas a larger loss of entropy takes place in the sleeve at these areas, in other words the molecule chains are stretched, which in turn decreases their mobility, the soft sleeve becomes harder in the sensitive areas.

Elastic materials harden when they are stretched, but in the case above an uneven hardening will be achieved where the harder portions are placed at the portions being most stressed, which results in discomfort and the user being chafed.

Most of the users of prosthetic devices are lower leg amputated and elderly and therefore do sit quite a lot when they use their prosthetic device. The problem of the frequently seen soft prosthetic sleeves of today is that they fold at the back of the knee when the knee is bent, which results in discomfort and being chafed and, in the worst case, that the flow of blood is obstructed and that a so called stasis condition arises. Note in FIG. 4 how the sleeve is folded at its upper right portion.

Therefore there is a need of a prosthetic sleeve for which the disadvantages mentioned above will be avoided to thereby for an amputated patient create an aiding prosthetic means which presents a good flexibility but at the same time provides a good stability.

SHORT DESCRIPTION OF THE INVENTION

The disadvantages described above are solved by means of a prosthetic sleeve according to the present invention. The new prosthetic sleeve according to the invention constitutes a sleeve member having a conical shape where one end is open and the other completely closed with a somewhat rounded shape. The sleeve member which is made of a thermoplastic elastomer (TPE material) may be formed with heat and is transparent, soft and kind to the skin, which results in that it better can be adapted to any amputation stump.

BRIEF DESCRIPTION OF THE DRAWINGS

Below the invention will be described in detail by means of the attached drawings in which.

DESCRIPTION OF EXEMPLIFYING EMBODIMENTS

Figure 1:
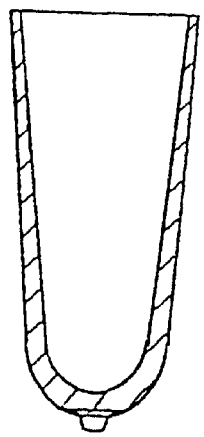
FIG. 1 shows a sleeve member according to the prior art.

A conical elastic sleeve member similar to the one demonstrated in FIG. 1 is rolled, according to the method of the invention, over a copy of the stump from the amputated extremity. The copy in the example has a shape, demonstrated in FIG. 2, corresponding to a knee with a lower leg stump. The sleeve member according to the invention consists of a thermoplastic elastic material which is characterized by being able to be formed by means of heat. A preferred polymeric material as such is transparent, soft and kind to the skin and elastic and for instance a thermoelastic based on a Styrene-Ethylene/Butadiene-Styrene Block-copolymer (SEBS) and intended for injection moulding and extrudation, as for instance the TPE material DRYFLEX® 500120 from Nolato Elasteknik, Torekov, Sweden. The copy of the extremity having the sleeve member of the invention applied is heated in a suitable manner, for instance in an oven. When the sleeve member on the copy of the stump is heated it will form itself after the copy of the extremity and the best possible adaption of a sleeve member to the extremity is achieved according to FIG. 5. When the sleeve cools it crimps slightly, but keeps its shape after being removed from the copy of the extremity, which is demonstrated in FIG. 6. This will provide the best comfort for the user of the prosthetic device as the uneven distribution of pressure and folding demonstrated in FIG. 4 will be avoided, and which normally otherwise would be obtained with a sleeve according to the state of the art.

Figure 9:
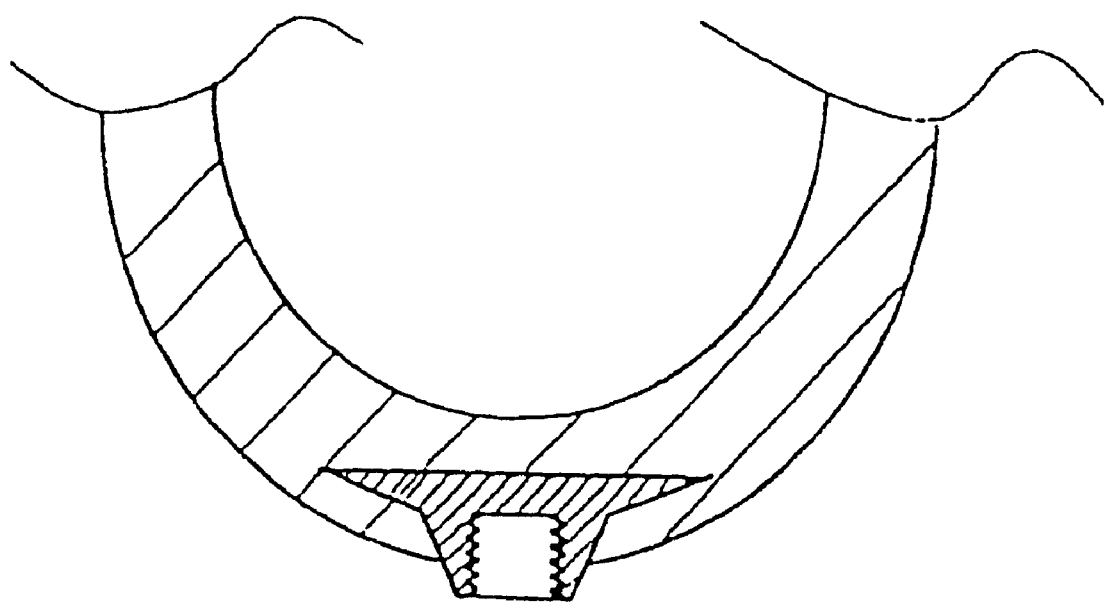
FIG. 9 shows an enlarged view of the lower portion of a sleeve member according to FIG. 7 having a molded fixing for a prosthetic device.

As the elastic sleeve now has been adapted to the amputation stump, a smooth compression is achieved over the entire ampulation stump, which in this manner provides a good suspension without producing localized pressure stresses. The stretching of the sleeve member also is equal in all portions, which gives an even and proportionately small loss of entropy, in other words the sleeve maintains itself soft and elastic in all portions, which considerably decreases the risk of being chafed. To obtain a good and safe fixation between the soft inner sleeve and a hard outer sleeve the soft inner sleeve is provided with a distal attachment device which easily is threaded onto different holders available on the market. Such a distal holder is demonstrated in FIG. 9.

Figure 4:
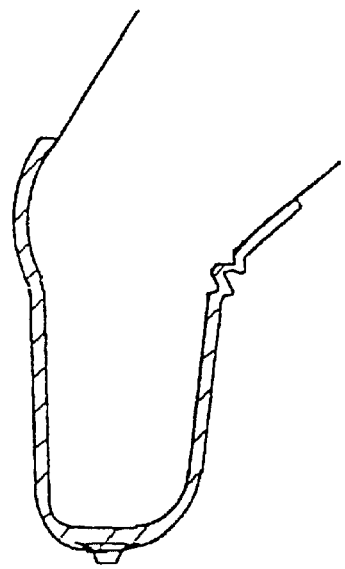
FIG. 4 shows how a sleeve member according to the prior art will fold after application to an amputation stump according to FIG. 2.
Figure 5:
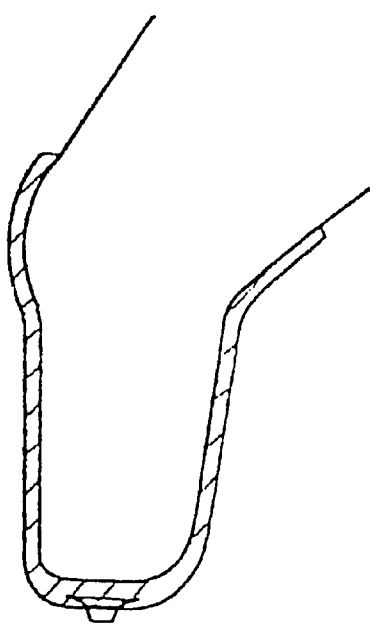
FIG. 5 shows how the sleeve member according to the present invention forms to the amputation stump.

Another advantage is that the sleeve member according to the present invention may be formed after e.g. a flexed (bent) knee which makes it easy to avoid the foldings which otherwise would arise at the back of the knee when sitting down, compare for instance FIG. 4 and FIG. 5. This essentially improves the comfort for a person carrying such a prosthetic device.

Still another advantage of a prefabricated conical elastic sleeve member according to the present invention is that it is not necessary to hold so many sizes in stock as the size of the sleeve is easily changed with heat.

For instance if a stress-relief must be provided around prominences, such a stress-relief may be simply achieved by using a piece of same material which by means of heat is fused together with the outer surface of the soft inner sleeve, whereby this accomplishes a locally thicker area of the soft inner sleeve.

Figure 7:
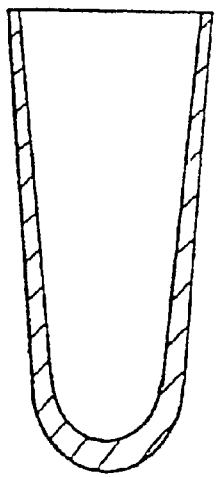
FIGS. 7 and 8 show the sleeve member according to the invention to be combined to obtain one type of material towards the amputation stump and another material outwards.
Figure 8:
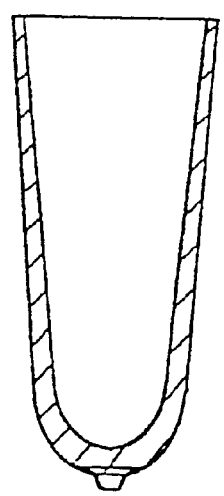

If it is desirable that the entire sleeve should be thicker it is simply possible to put a first soft inner sleeve according to FIG. 7 and a second soft sleeve according to FIG. 8 into each other and heat these into one. This also results, if a sleeve having a better scratch and abrasion strength is desirable in a particular application, that it is also possible to heat a somewhat harder sleeve of similar material to the inner soft elastic sleeve. Thus, this gives a softer sleeve towards the part of the body and outwards a harder sleeve, which increases its strength.

Additionally it is also possible to mix heat conducting material in the soft sleeve, which thereby will not be so warm. By mixing color particles in the thermoplastic elastomer material of the sleeve member the sleeve may simply be slightly colored instead of being completely transparent.

Description Step by Step of the Application of the Sleeve

Figure 2:
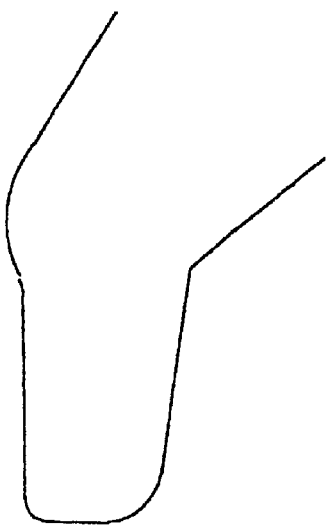
FIG. 2 demonstrates a copy of an amputation stump onto which the sleeve member according to FIG. 1 is positioned.

First a casting is made, for instance according to FIG. 2, of the body part to be provided with a prosthetic device. This may take place by means of plaster bandage or alternatively by means of an imaging so called laser scanner.

The hardened plaster bandage forms a negative mould of the stump. The mould is the filled with plaster which becomes rigid and forms a copy of the stump. In the same manner a computer controlled cutter may in a suitable material create a copy of the stump aided by the data read by means of the laser scanner equipment. This is also done today irrespective of type of sleeve.

Figure 3:
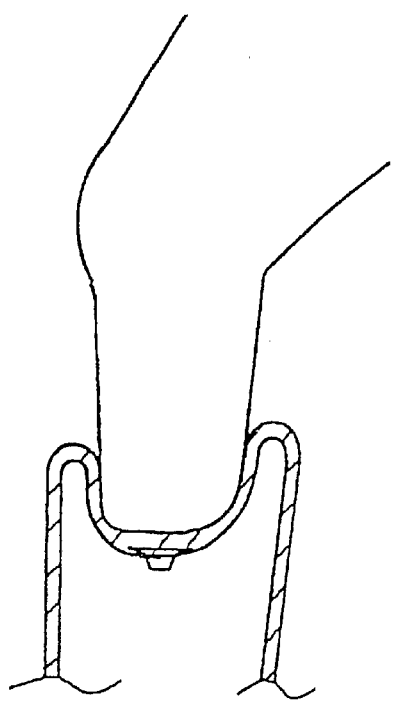
FIG. 3 demonstrates how the sleeve member is rolled onto the amputation stump according to FIG. 2.

The copy of the stump is measured and a suitable elastomer inner sleeve according to the present invention is rolled onto the copy of the stump (also see FIGS. 3 and 4).

The copy of the stump and the soft sleeve with stress-relieving material is put into a hot oven and is heated during a few minutes, which results that the sleeve of thermoplastic elastic material will form after the copy of the amputation stump.

The edges then in an ordinary way are trimmed, for instance by means of a pair of scissors, which is also done with sleeves according to the state of the art. If upon testing the result is not satisfying, it is afterwards simple to make small adjustments. If the appearance of the amputation stump changes somewhat, corresponding changes are performed to the previous copy, which then again is provided with the sleeve and heated, whereby after cooling the sleeve will maintain the new small changes.

If it upon testing is noted that there must be made some further stress-relief, this is done by using a piece of same material, which by means of heating is fused to the outer surface of the soft inner sleeve. It is then created a locally thicker area on the soft inner sleeve for further stress-relief.

Figure 6:
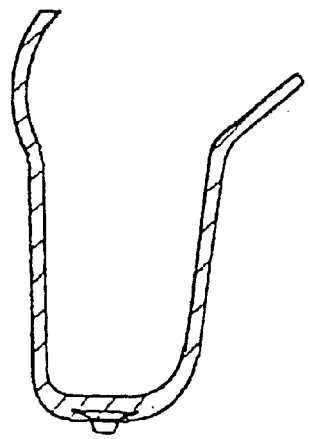
FIG. 6 shows how the sleeve member according to the present invention maintains its given shape after removal from the copy of the amputation stump according to FIG. 2.

The specifically adapted soft sleeve according to the present invention then is ready (see FIG. 6). Note the difference to the conventionally utilized sleeve of today according to FIG. 4, when it is used for the patient. When the sleeve according to the invention, in the example above, is not used for the patient it consequently has an appearance according to FIG. 6, while a sleeve according to the prior art being only elastic returns to an appearance according to FIG. 1.

Another problem of amputation stumps is the treatment after amputation up to prosthetic provision, as well as when the prosthetic user, from different reasons, is not able to use his prosthetic device. It is important that the function and shape of the body remain is maintained to facilitate the use of a prosthetic device.

An ordinary post-operative routine therefore is to daily wrap the amputation stump with bandage aiming to counteract swelling. It is then important that the wrapping is done correctly, otherwise a wrapping may have the opposite effect.

Having a silicon sleeve according to the state of the art, for example according to the patent SE 454 943, the elastic conically shaped sleeve gives a compression over the stump which is uneven as no amputation stump is conically shaped, which in unfavorable cases may lead to obstruction of the blood flow. Another problem with this is that its relatively high elasticity in radial direction and relatively low elasticity in axial direction lead to poor control of the distal axial compression.

In the case according to the prior art the stump is compressed somewhat along the conical shape of the sleeve, but as the control of the distal compression is poor due to the sleeve being relatively inelastic in the axial direction, this leads to giving the patient an incorrect distal compression of the amputation stump, which in turn results in that the amputation stump may distally swell. This increase of soft portions in the distal end of the amputation stump implies that the patient will not get an optimal prosthetic provision.

In this context the so called Alpha sleeve, referred to above, will actually be inappropriate, as in a post-operative period you will be dependent of seeing the stump inside the sleeve to ensure that the adaption gives a correct compression.

The conical elastic sleeve member according to the invention which is slipped over the copy of the extremity which it should be attached to, and is heated, whereby it forms after the copy of the extremity and will result in the best possible adaption of a sleeve to the remaining extremity. When the sleeve cools it crimps slightly, but maintains the shape of the extremity. When the sleeve then is used in a post-operative aiming to counteract swelling, it gives an even compression over the entire amputation stump, which is simple to control through this transparent sleeve member, and which results in an amputation stump being easy to prosthetically provide and gives the prosthetic user a better comfort.

A further advantage of the sleeve member according to the present invention is that it is simple to afterwards perform small adjustments. If the amputation stump somewhat changes appearance, the corresponding changes are performed to the earlier copy and the sleeve member is again slipped onto the copy and heated, whereby after cooling it will maintain the new small changes.

Still a further advantage of the present invention is that contrary to conventionally made sleeves normally being more or less stiff and therefore during forming needing a method using low pressure or vacuum to be able to form after the model, the present initial sleeve being elastic all the time will perfectly follow the shape of the model. The present method does not include a step of crimping like most earlier methods using vacuum, but is merely a heating and cooling, whereby the sleeve after cooling "remembers" the form of the model.

What is claimed is:

1. A method of producing a prosthetic sleeve that conforms to a true shape of an amputated limb of an amputee's arm or leg, comprising the steps of:

forming a true copy of said amputated limb;

providing an initial conical sleeve element of a thermoplastic elastomer material having a larger, open end for insertion of the amputated limb and a narrower, closed end for attachment of a prosthetic device;

slipping the conical sleeve element over the copy;

heating the copy and the sleeve element to a temperature at which the sleeve element will adapt to the shape of the copy; and leaving the thermally shaped sleeve for cooling on the copy before removal of the thermoformed, elastic sleeve.

2. The method of claim 1, wherein the thermoplastic elastomer material is a styrenic block-copolymer.

3. The method of claim 2, wherein the thermoplastic elastomer material is a Styrene-Ethylene-Butadiene-Styrene block-copolymer (SEBS).

* * * * *

UNITED STATES PATENT AND TRADEMARK OFFICE
CERTIFICATE OF CORRECTION

PATENT NO. : 6,440,345 B1
DATED : August 27, 2002
INVENTOR(S) : Kennet Hellberg

It is certified that error appears in the above-identified patent and that said Letters Patent is hereby corrected as shown below:

<u>Title page,</u>
Amend Item [22], to read as follows:

-- [22] PCT Filed:  March 25, 1998 --.
add Item [86] and [87] as follows:

-- [86]  PCT No.:  PCT/SE98/00543

§ 371(c) (1),
(2), (4) Date:  Oct. 15, 1999 --.

-- [87]  PCT Pub. No.:  WO98/48741
PCT Pub. Date:  Nov. 5, 1998 --.

Signed and Sealed this

Seventh Day of January, 2003

JAMES E. ROGAN
*Director of the United States Patent and Trademark Office*